United States Patent [19]
Egan

[11] Patent Number: 5,941,901
[45] Date of Patent: Aug. 24, 1999

[54] BONDABLE EXPANSION PLUG FOR SOFT TISSUE FIXATION

[75] Inventor: Thomas D. Egan, Marblehead, Mass.

[73] Assignee: Axya Medical, Inc., Beverly, Mass.

[21] Appl. No.: 09/061,604

[22] Filed: Apr. 16, 1998

[51] Int. Cl.⁶ .................................................. A61B 17/04
[52] U.S. Cl. ................................ 606/232; 606/68; 606/72
[58] Field of Search ........................ 606/232, 72, 68, 606/73, 75

[56] References Cited

U.S. PATENT DOCUMENTS

| | | | |
|---|---|---|---|
| 5,489,210 | 2/1996 | Hanosh | 433/173 |
| 5,593,425 | 1/1997 | Bonutti et al. | 606/232 |
| 5,643,321 | 7/1997 | McDevitt | 606/232 |
| 5,649,963 | 7/1997 | McDevitt | 606/232 |
| 5,707,395 | 1/1998 | Li | 606/232 |
| 5,782,865 | 7/1998 | Grotz | 606/232 |
| 5,797,963 | 8/1998 | McDevitt | 606/232 |
| 5,843,127 | 12/1998 | Li | 606/232 |

*Primary Examiner*—Michael Buiz
*Assistant Examiner*—Tina T. D. Pham
*Attorney, Agent, or Firm*—Lappin & Kusmer LLP

[57] ABSTRACT

An expandable soft tissue fixation assembly for use in anchoring soft tissue to bone. The assembly includes a tab connected to an anchor, a sleeve adapted to surround the anchor, and a flange adapted to hold a soft tissue segment next to a bone. The sleeve is inserted into a blind hole in a bone, and a section of soft tissue is placed over the hole next to the bone. Energy is applied to the flange while a predetermined axial tension is applied to the tab to compress a flared portion of the anchor against the sleeve. An upper tube portion of the anchor and the flange are bonded together, and the applied axial force on the tab separates it from the anchor, leaving the assembly anchored in the bone and the soft tissue section anchored in place between the flange and the bone.

3 Claims, 2 Drawing Sheets

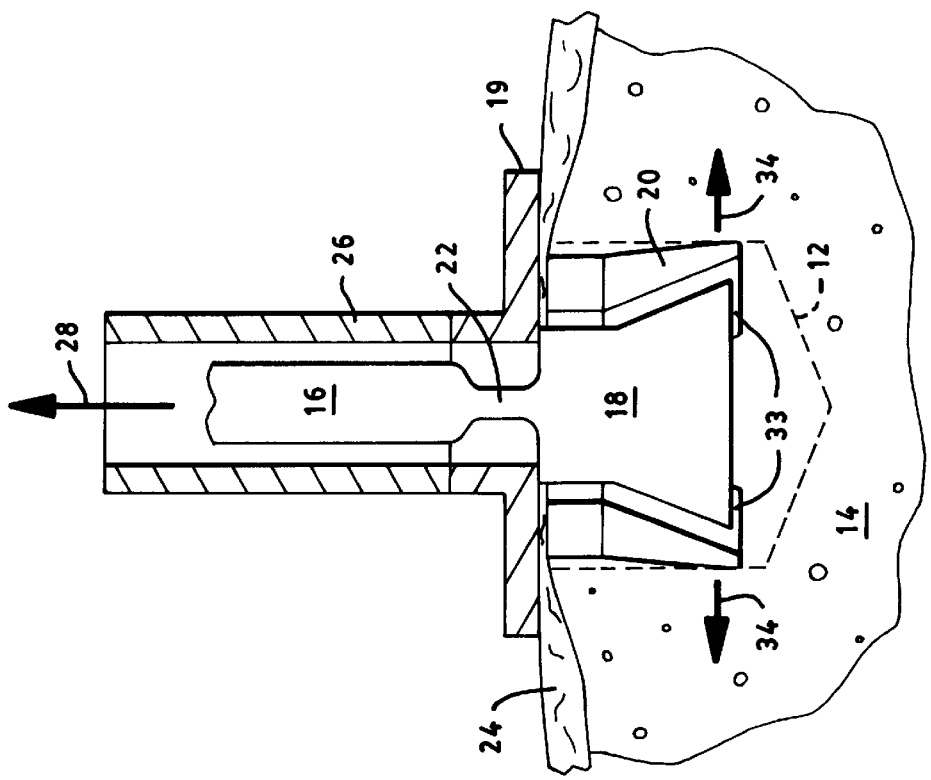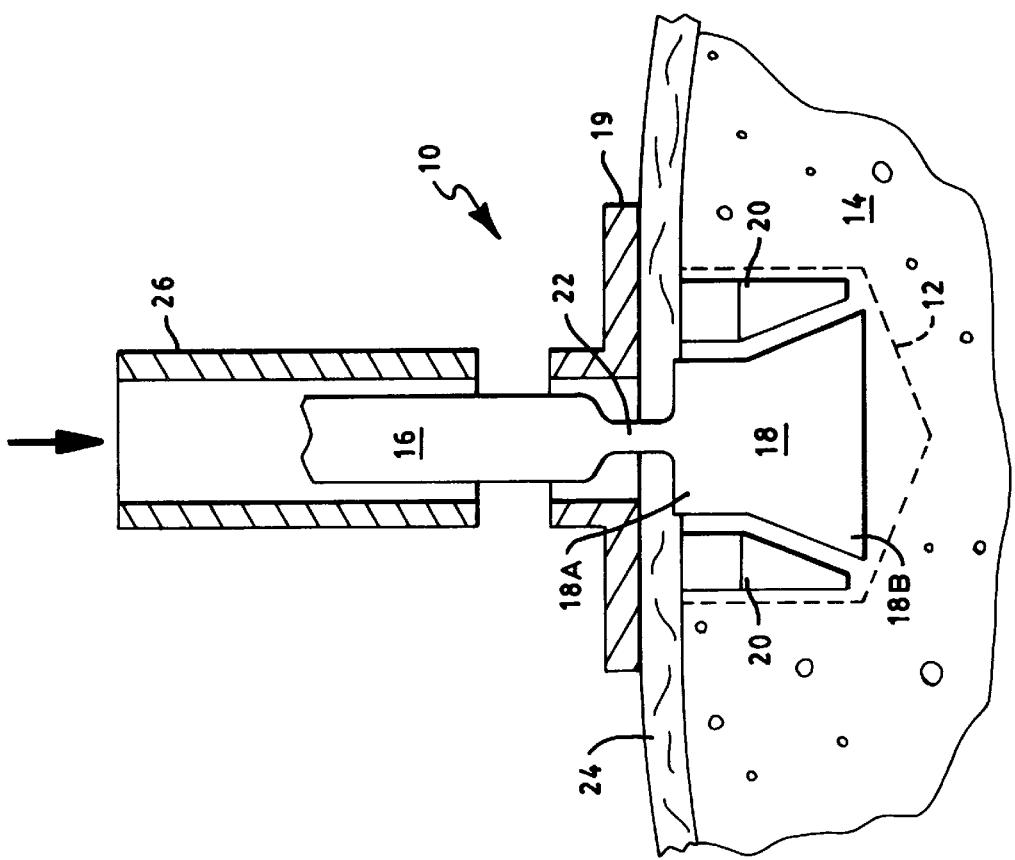

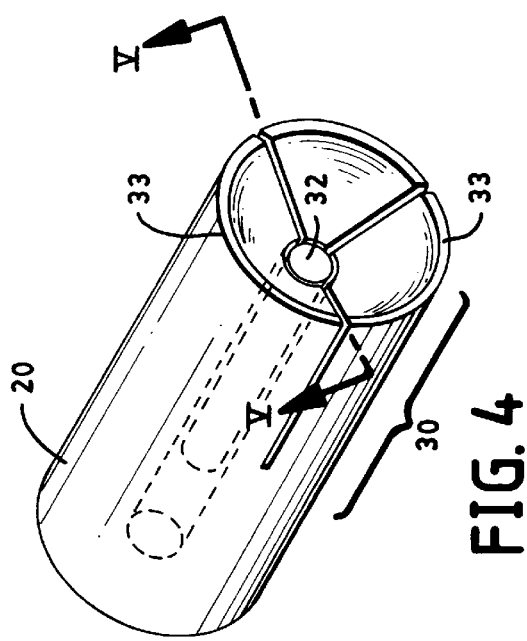
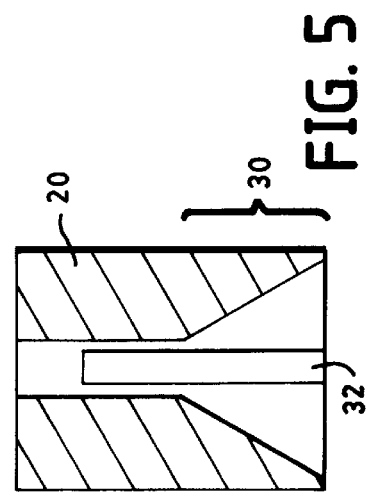
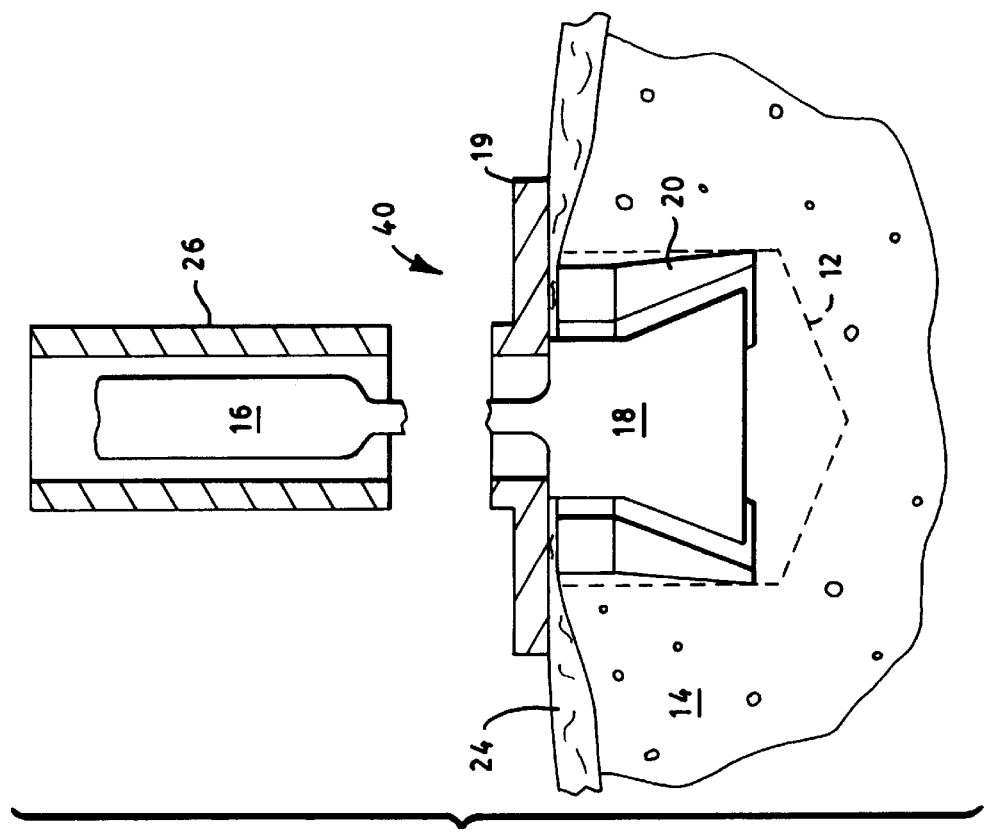

BONDABLE EXPANSION PLUG FOR SOFT TISSUE FIXATION

FIELD OF THE INVENTION

The present invention relates to surgical soft tissue fixation devices, and more particularly to expandable soft tissue fixation devices which are suitable for use in attaching soft tissue to a blind hole in a bone.

BACKGROUND OF THE INVENTION

U.S. Pat. No. 5,593,425 to Bonutti et al. discloses a heat-bondable, expandable surgical anchor for fastening soft tissue to a blind hole in a bone. One embodiment of the device, shown in FIGS. 9A–9D of Bonutti et al., includes an expandable anchor portion, a suture extending from the anchor, and a heat bondable fastener portion which is bonded to the suture to lock the anchor in place. Another embodiment, shown in FIGS. 11A–11C, is a rivet fastener including a sleeve and a headed mandrel which extend into a blind hole in a bone through the tissue to be anchored. The mandrel is pulled through the sleeve, which is held stationary, so that the head spreads the rear portion of the sleeve to lock it in place in the bone. The end of the mandrel is cut off and heat bonded to fix the anchor in place.

The Bonutti et al. devices are deployable in a blind hole in a bone but require a final heat bonding step to lock the devices in place. It would be advantageous to provide an expandable soft tissue anchoring device which is fully deployable in a single step.

SUMMARY OF THE INVENTION

According to the invention, there is provided an expandable soft tissue fixation assembly. The assembly comprises:

a tab extending along an axis and connected, via a connecting region, to an anchor having a tube portion and a flared portion, the tube portion having a diameter D;

a sleeve adapted to surround the anchor and including multiple sections which can be expanded radially outward upon application of a force thereto; and a tubular flange having an inner bore of a diameter which is smaller than D. The flange is adapted to hold and distribute pressure over a section of soft tissue between the flange and a bone surface. The walls of the bore of the tubular flange interferingly engage with the walls of the tube portion of the anchor, so that the bore walls and tube portion walls form a shear weld upon application of sufficient energy to the tubular flange. Concurrent application of a predetermined tensile force to the tab along the axis of the tab compresses the flared portion of the anchor against the sleeve, thereby radially extending the multiple sections of the sleeve. The compression force anchors the flared portion and the sleeve in the bone and holds the soft tissue section between the flange portion and the bone. It also causes the tab to separate from the flared portion of the anchor.

At least the flange and the flared portion of the anchor are made of a bondable thermoplastic material. In a preferred embodiment, ultrasonic energy is applied to the flange to bond the flange to the flared portion of the anchor.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 1 is a sectional view of an assembly according to the invention, in which the assembly is installed in a blind hole in a bone in preparation for welding of the flange and flared portion of the anchor;

FIG. 2 is a sectional view of the assembly after ultrasonic welding of the flange and flared portion of the anchor;

FIG. 3 is a sectional view of the assembly after the tab has been separated from the flared portion of the anchor;

FIG. 4 is a perspective view of the sleeve portion of the assembly; and

FIG. 5 is a sectional view of the sleeve along section lines V–V.

Like elements in the respective FIGURES have the same reference numbers.

DETAILED DESCRIPTION OF THE PREFERRED EMBODIMENTS

The assembly 10 of the present invention comprises a bondable, expandable device which can be installed in a blind hole 12 in a bone 14 to anchor it in the bone. Such an anchor can be used to fasten soft tissue, such as ligaments and tendons, to bone. The assembly includes three separate pieces, two of which are bonded together in situ in a single step to form a unitary soft tissue anchor.

The assembly 10 includes a main tab 16 connected to an anchor 18 having a tube portion 18A and a flared portion 18B, a separate flange 19, and a separate sleeve 20 which fits around the anchor, as shown in FIG. 1. The tab 16 is connected to the tube portion 18A of the anchor by a connecting region 22 which, as detailed more fully below, is designed to separate under an applied predetermined tensile force after the sleeve 20 and anchor 18 are joined together. The flange 19 rests on the section of soft tissue 24 placed adjacent to the surface of the bone 14 and distributes force against the bone over the surface area of the flange.

The assembly is designed to be ultrasonically welded in situ upon application of ultrasonic energy to the anchor by a tubular ultrasonic welding horn 26. Prior to welding, the sleeve 20 is inserted into a predrilled hole 12 in the bone 14. The tissue 24 to be held in place next to the bone is placed over the hole with the sleeve in it, and the flange 19 is placed over the tissue section 24 and aligned with the underlying hole. The tubular ultrasonic weld horn 26 is brought into contact with the flange 19 and compressed against the flange, thereby compressing the tissue 24 to the bone surface. As shown most clearly in FIG. 1, the outer diameter of the tube portion 18A of the anchor is sufficiently greater than the inner diameter of the flange 19 to establish an interference between the walls of the flange and the tube portion of the anchor. The flange 19 receives ultrasonic energy from the horn 26 and vibrates relative to the tube portion 18A of the anchor, which abuts the bone and thus serves as a stationary anvil. The tube portion 18A and the flange 19 melt locally at their respective interference points and bond together in a shear weld, as shown in FIG. 2.

During ultrasonic welding of the tube portion and flange, the tab 16 is grasped by a non-ultrasonically activated grasper (not shown) and pulled in the direction of arrow 28 to compress the tube portion and flange together, clamping the tissue section 24 between them. This compression pulls the anchor up, thereby radially distending the multipart sections of the sleeve 20 and lodging the flared portion 18B of the anchor in the sleeve 20 against the sides of the hole 12 in the bone 14. At some predetermined tensile force the connecting region 22 between the tab 16 and the tube portion 18A fails, causing the tab 16 to separate from the welded tube/flange. The connecting region 22 is designed to fail in tension at a predetermined force and is accordingly necked down, scored or otherwise constructed to accomplish this objective. The fully deployed assembly 40, shown in FIG. 3, includes the welded tube/flange and the distended sleeve 20. The tissue section 24 is firmly held between the flange 19 and the bone 14.

The sleeve 20 is shown in greater detail in FIGS. 4 and 5. A bottom portion 30 of the sleeve is separable into multiple flared sections 33 which can be distended radially out from the bore 32 upon application of a force against the sections. The bore 32 of the sleeve is sized to accommodate the flared portion 18B of the anchor, as shown in FIG. 1, and the axial force applied to the tab 16 causes the flared portion 18B to press radially against the sleeve 20, as shown by arrows 34 in FIG. 2.

At least the tube portion 18B and the flange 19 are made of a material, such as a thermoplastic, which can be bonded together upon the application of ultrasonic or thermal energy thereto. The sleeve 20 can be, but need not be, made of a material which can be ultrasonically welded, as it is joined to the anchor 18 by virtue of a compression fit and not a thermal bond.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

I claim:

1. An expandable soft tissue fixation assembly, comprising:

a tab extending along an axis and connected, via a connecting region, to an anchor having a tube portion and a flared portion, the tube portion having a diameter D;

a sleeve adapted to surround the anchor and including multiple sections which can be expanded radially outward upon application of a force thereto; and a tubular flange having an inner bore of a diameter which is smaller than D;

wherein the flange is adapted to hold and distribute pressure over a section of soft tissue between the flange and a bone surface, wherein the walls of the bore of the tubular flange interferingly engage with the walls of the tube portion of the anchor, so that the bore walls and tube portion walls form a shear weld upon application of sufficient energy to the tubular flange, wherein concurrent application of a predetermined tensile force to the tab along the axis of the tab compresses the flared portion of the anchor against the sleeve, thereby radially extending the multiple sections of the sleeve, anchoring the flared portion and the sleeve in the bone, holding the soft tissue section between the flange and the bone, and causing the tab to separate from the tubed portion of the anchor.

2. An assembly according to claim 1, wherein at least the flange and the tubed portion of the anchor are made of a bondable thermoplastic material.

3. An assembly according to claim 2, wherein ultrasonic energy is applied to the flange to bond the flange to the tubed portion of the anchor.

* * * * *

UNITED STATES PATENT AND TRADEMARK OFFICE
CERTIFICATE OF CORRECTION

PATENT NO. : 5,941,901
DATED : August 24, 1999
INVENTOR(S) : Thomas D. Egan

It is certified that error appears in the above-identified patent and that said Letters Patent is hereby corrected as shown below:

Claim 1, line 26, delete "tubed" and insert therefor, --tube--.
Claim 1, line 29, delete "tubed" and insert therefor, --tube--.
Claim 1, line 32, delete "tubed" and insert therefor, --tube--.

Signed and Sealed this

First Day of February, 2000

Attest:

Q. TODD DICKINSON

Attesting Officer

Acting Commissioner of Patents and Trademarks